United States Patent
Huang

(10) Patent No.: US 7,273,628 B2
(45) Date of Patent: Sep. 25, 2007

(54) METHOD FOR REMOVING AFLATOXINS FROM CHINESE HERBAL MEDICINES

(75) Inventor: Ho Shin Huang, Tainan Hsien (TW)

(73) Assignee: Kaiser Pharmaceutical Co., Ltd., Yung Kang, Tainan (TW)

( * ) Notice: Subject to any disclaimer, the term of this patent is extended or adjusted under 35 U.S.C. 154(b) by 0 days.

(21) Appl. No.: 11/269,049

(22) Filed: Nov. 9, 2005

(65) Prior Publication Data

US 2007/0031448 A1 Feb. 8, 2007

(51) Int. Cl.
*A01N 65/00* (2006.01)
*A61K 36/00* (2006.01)

(52) U.S. Cl. ..................................................... 424/725

(58) Field of Classification Search .................... None
See application file for complete search history.

(56) References Cited

OTHER PUBLICATIONS

Klaus Reif, Wolfgang Metzger, Determination of alfaxotins in medicinal herbs and plant extracts, 1995, Journal of Chromatography A, 692, 131-136.*

* cited by examiner

*Primary Examiner*—Susan Coe Hoffman
*Assistant Examiner*—Catheryne Chen

(57) ABSTRACT

A method for removing aflatoxins from Chinese herbal medicines comprises the steps of grinding a predetermined Chinese herbal medicine and submerging it into an amount of alcohol solvent twice as much as the dry weight of the medicine and using water to flush away the alcohol solvent from the medicine after a being submerged for a predetermined period of time. The Chinese herbal medicine is then dried to reduce its water content. The above steps are repeated at least twice so as to reduce its aflatoxins under a safety level.

8 Claims, 5 Drawing Sheets

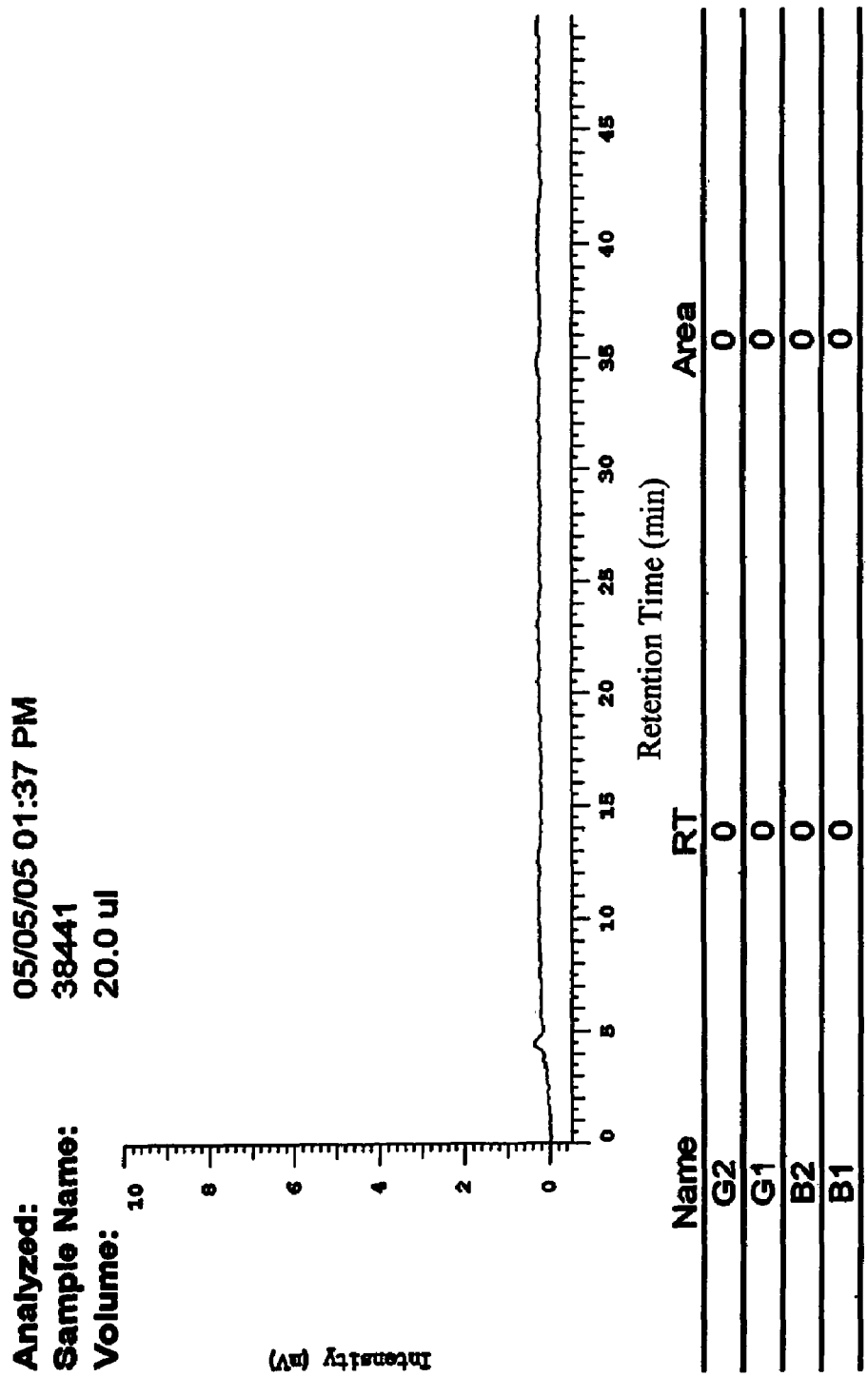
Fig. 2 *Corydalis yanhusuo*

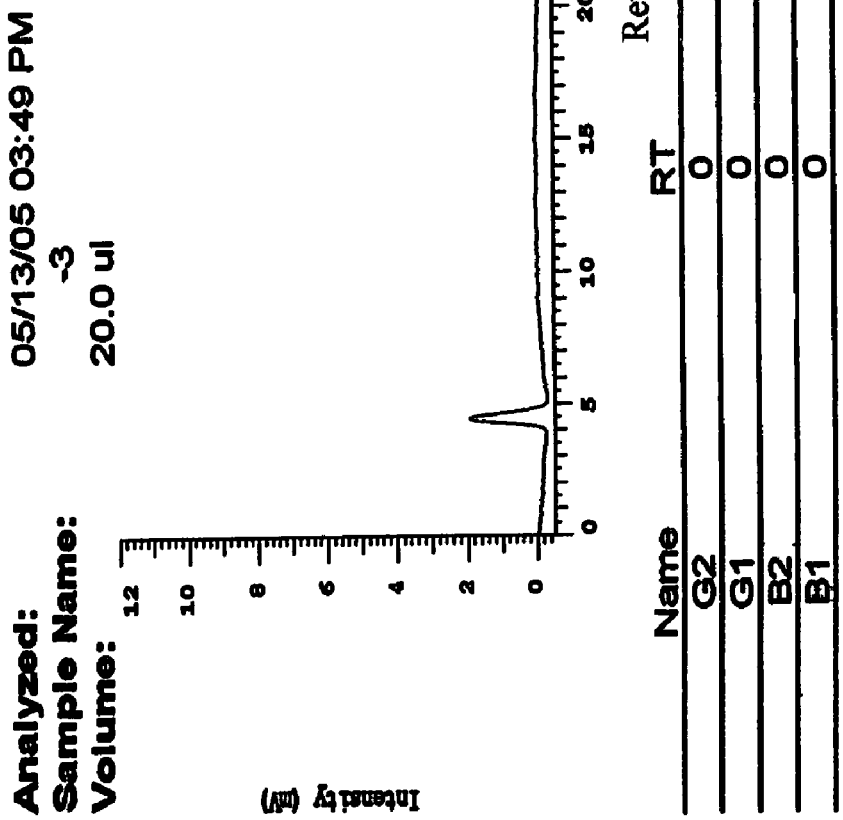
Fig. 3: → specimen → method

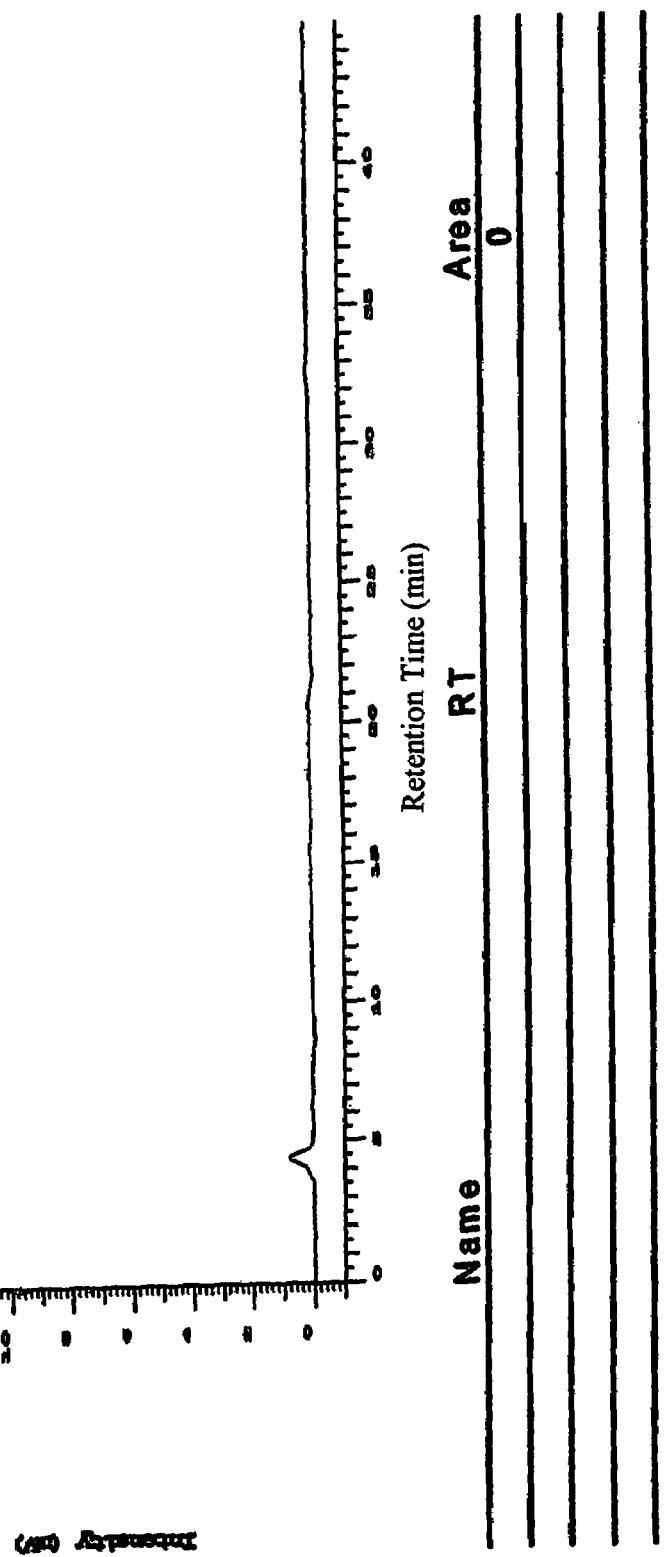
Fig. 4: → *Cyperus rotundus* →method

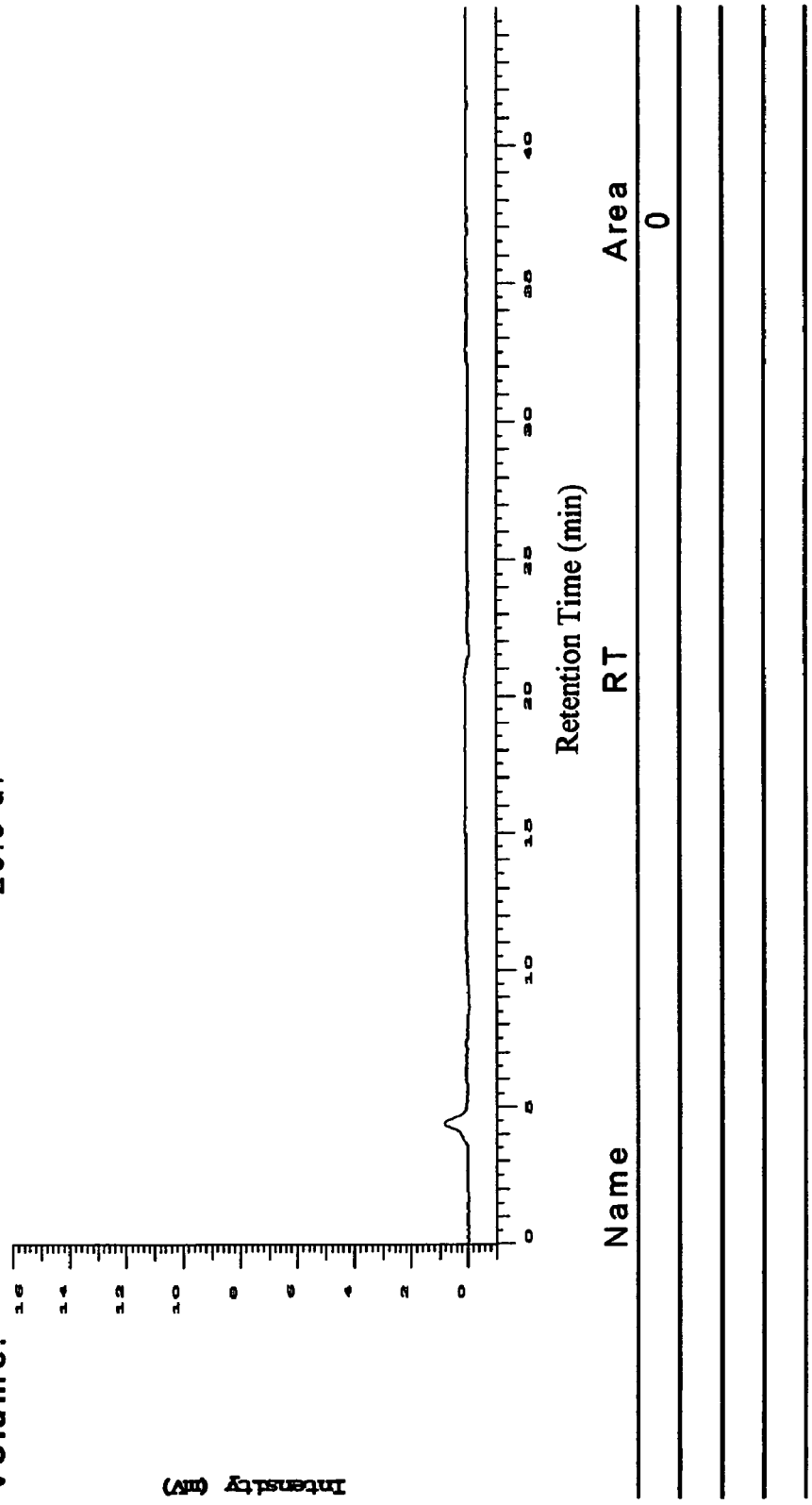
Fig. 5 → dried citrus peel →method

METHOD FOR REMOVING AFLATOXINS FROM CHINESE HERBAL MEDICINES

FIELD OF THE INVENTION

The present invention relates to the removal of aflatoxins, more particularly to a method for removing aflatoxins from Chinese herbal medicines by means of firstly mixing Chinese herbal medicines with alcohol in a polar solvent and then extracting the aflatoxins therein.

BACKGROUND OF THE INVENTION

Aflatoxins are toxic secondary metabolites produced by fungi *Aspergillus Flavus* Link and *A. Parasiticus* Speare, which are classified into $B_1$, $B_2$, $G_1$ and $G_2$ types. The fungi *Aspergillus Flavus* Link mainly produce $B_1$ and $B_2$ types, whereas the fungi *A. Parasiticus* produce $G_1$ and $G_2$ types, in addition to $B_1$ and $B_2$ types. Among those types, $B_1$ type is the most vicious carcinogenic substance.

Taking food and Chinese herbal medicines polluted with aflatoxins of high concentration may lead to diseases of hepatotoxicity, teratogenicity or immuno-supression, sometimes leading to deaths. Further, the food poisoning caused by aflatoxins, Aflatoxin-cosis, is a liver disease characterized by vomit, stomachache, spastic, pulmonary edema, coma or store fat in liver, kidney and heart or hydrocephalus, which may result in deaths. It is found, in the African and Asian epidemiological studies, that people in the regions of higher levels of aflatoxins pollution are more susceptible to liver cancer. Further, atlatoxins are a cause why B-type hepatitis virus carriers develop liver cancer.

To avoid endangering human health, the conventional method for suppressing aflatoxins is storing food or Chinese herbal medicines in a fungi-unfriendly environment, such as places of low humidity, whereby the chance for fungi growth is suppressed, and aflatoxins produced during the proliferation and metabolism of fungi become limited. Therefore, the chance of aflatoxin pollution on food become low. We can also remove the aflatoxin pollution by a mechanical means, which is particularly applied to remove the polluted portions of food contraindicated by aflatoxins. Thereby, unpolluted portions of food or Chinese herbal medicines can be kept for future consumptions. Further, the toxicity of aflatoxins can be damaged by alkali-added solvents and reduced to safety level.

However, the storage of food or Chinese herbal medicines in a dry space, though being capable of suppressing fungi growth, will cause management problem if it lasts for a long period of time. Similarly, the mechanical removal of aflatoxins by taking away polluted portions of food cannot guarantee that the remained portions is not polluted by aflatoxins. Especially, it cannot recognize the portions covered by the expansion of the pollution. Finally, the addition of alkali substances into a solvent and then reducing of the toxicity of aflatoxins in food may cause harmful quality changes of the food.

Therefore, the conventional methods of suppressing aflatoxins in food or Chinese herbal medicines have at least the following disadvantages.

1. The incomplete removal by the mechanical means;
2. The effect of chemical substances left during the toxicity reduction of aflatoxin by alkali-added solvents on human health.

SUMMARY OF THE INVENTION

Accordingly, the primary objective of the present invention is to provide a method for removing aflatoxins from Chinese herbal medicines, which uses simple instruments, is of low production cost and further leaves no poisonous substances in the Chinese herbal medicines during this process. A predetermined amount of alcohol solvent is used to mixed extract the aflatoxins in a processed Chinese herbal medicine, since the solvent is relatively harmless and hard to be left in the Chinese herbal medicine after the extraction. Since the aflatoxins in the processed Chinese herbal medicine are capable being solvable in the alcohol solvent, the solvent is an ideal solvent for extracting the aflatoxins. A Chinese herbal medicine is ground into powder for increasing the contact area between the medicine and the solvent, whereby the rate of removal of aflatoxins will be enhanced. After repeated rinsing the medicine, the aflatoxins therein will be extracted rapidly.

The secondary objective of the present invention is to provide a method for removing aflatoxins from Chinese herbal medicines that will assure the safety of a Chinese herbal medicine because the aflatoxins to be extracted and removed are a cancer inducing substance and hard to be destroyed by high temperature. Aflatoxins can induce liver diseases, therefore being harmful to human health.

The present invention utilizes the aflatoxin-extracting capability of an amount of alcohol solvent and the enhancement of contact area between the solvent and a Chinese herbal medicine by grinding the medicine. Further, a repeated process of removing the solvent from the medicine will quickly take away the aflatoxins therein. The method is so simple as to largely reducing the cost of aflatoxin removal.

The various objects and advantages of the present invention will be more readily understood from the following detailed description when read in conjunction with the appended drawings.

BRIEF DESCRIPTION OF THE DRAWINGS

FIG. 2 shows two charts indicating the aflatoxin content in the specimen of *Corydalis yanhusuo* respectively before and after a process disclosed by the present invention.

FIG. 3 shows two charts indicating the aflatoxin content in the specimen of *Corydalis yanhusuo* respectively before and after another process disclosed by the present invention.

FIG. 4 shows two charts indicating the aflatoxin content in the specimen of *Cyperus rotundus* respectively before and after a process disclosed by the present invention.

FIG. 5 shows two charts indicating the aflatoxin content in the specimen of dried citrus peel respectively before and after a process disclosed by the present invention.

DETAILED DESCRIPTION OF THE PREFERRED EMBODIMENTS

Figure 1:
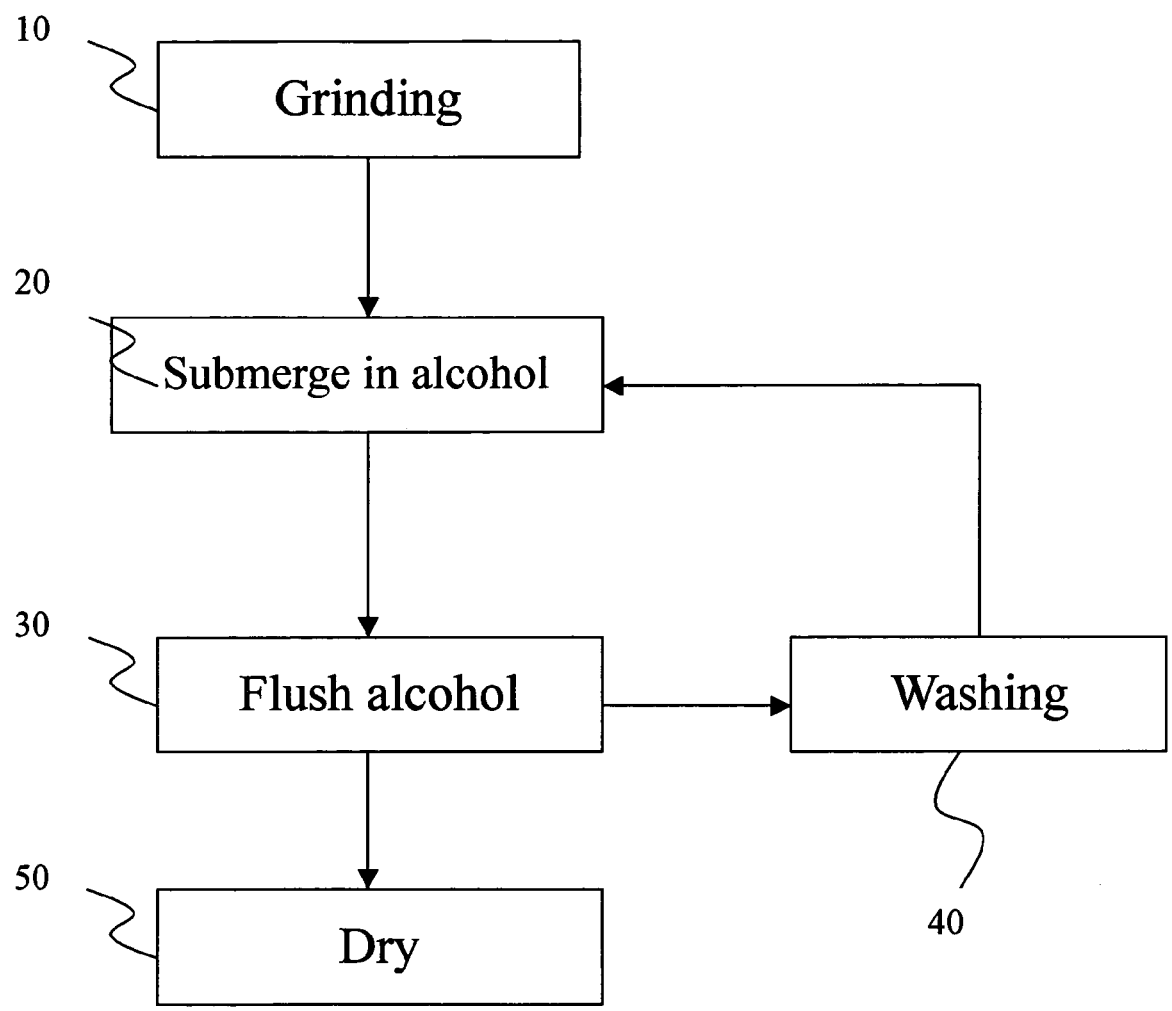
FIG. 1 is a flow chart for the method for removing aflatoxins from Chinese herbal medicines of the present invention.

A method for removing aflatoxins from Chinese herbal medicines according to the present invention comprises the steps of:

(A) grinding a predetermined Chinese herbal medicine and submerging it into an amount of alcohol solvent twice as much as the dry weight of the medicine;

(B) using water to flush away the alcohol solvent from the medicine after a being submerged for a predetermined period of time; and (C) repeating steps (A) and (B) at least twice.

The First Preferred Embodiment

Take a 50.3 g amount of unprocessed *Corydalis yanhusuo*, wherein a total of 2.960 ppb aflatoxins is contained. The Chinese herbal medicine is ground to 20-300 mesh sizes, washed by a large amount of water and then dried. The ground medicine is submerged in an alcohol solvent (95%) three times heavier than the weight medicine for 60 minutes, after which time the medicine is separated from the solvent and dried for 30 minutes. Then, the dried medicine is washed by a large amount of water and then dried again. The ground medicine is again submerged in an alcohol solvent (95%) three times heavier than the weight medicine for 60 minutes, after which time the medicine is placed into a oven at 70° C. temperature till the water content thereof becomes less than 12%. Then, the aflatoxin content is measure again, and we find it is 0 ppb.

Regarding the aflatoxins in the specimen of *Corydalis yanhusuo*, the precise amount is measured by a High Performance Liquid Chromatography, the difference in aflatoxin content before and after the process is shown in FIG. 2.

The Second Preferred Embodiment

Take a 50.1 g amount of unprocessed *Corydalis yanhusuo*, wherein a total of 1.111 ppb aflatoxins is contained therein and measured. The Chinese herbal medicine is ground to 20-300 mesh sizes, washed by a large amount of water and then dried. The ground medicine is submerged in an alcohol solvent (95%) twice heavier than the weight medicine for 60 minutes, after which time the medicine is separated from the solvent and dried for 30 minutes. Then, the dried medicine is washed by a large amount of water and then dried again. The ground medicine is again submerged in an alcohol solvent (95%) twice heavier than the weight medicine for 60 minutes, after which time the medicine is placed into a oven at 70° C. temperature till the water content thereof becomes less than 12%. Then, the aflatoxin content is measure again, and we find it is 0 ppb.

Regarding the aflatoxins in the specimen of *Corydalis yanhusuo* in the second preferred embodiment, the precise amount is measured by a High Performance Liquid Chromatography, the difference in aflatoxin content before and after the process is shown in FIG. 3.

The next preferred embodiment illustrates the method for removing aflatoxins from Chinese herbal medicines wherein the Chinese herbal medicine is *Cyperus rotundus*.

Third Preferred Embodiment

Take a 38.1 g amount of unprocessed *Cyperus rotundus*, wherein a total of 5.210 ppb aflatoxins is contained therein and measured. The Chinese herbal medicine is ground to 20-300 mesh sizes, washed by a large amount of water and then dried. The ground medicine is submerged in an alcohol solvent (95%) three times heavier than the weight medicine for 60 minutes, after which time the medicine is separated from the solvent and dried for 30 minutes. Then, the dried medicine is washed by a large amount of water and then dried again. The ground medicine is again submerged in an alcohol solvent (95%) three times heavier than the weight medicine for 60 minutes, after which time the medicine is placed into a oven at 70° C. temperature till the water content thereof becomes less than 12%. Then, the aflatoxin content is measure again, and we find it is 0 ppb.

Regarding the aflatoxins in the specimen of *Cyperus rotundus* in the third preferred embodiment, the precise amount is measured by a High Performance Liquid Chromatography, the difference in aflatoxin content before and after the process is shown in FIG. 4.

The next preferred embodiment illustrates the method for removing aflatoxins from Chinese herbal medicines wherein the Chinese herbal medicine is dried citrus peel.

Fourth Preferred Embodiment

Take a 50.0 g amount of unprocessed dried citrus peel, wherein a total of 127.20 ppb aflatoxins is contained therein and measured. The Chinese herbal medicine is ground to 20-300 mesh sizes, washed by a large amount of water and then dried. The ground medicine is submerged in an alcohol solvent (95%) three times heavier than the weight medicine for 60 minutes, after which time the medicine is separated from the solvent and dried for 30 minutes. Then, the dried medicine is washed by a large amount of water and then dried again. The ground medicine is again submerged in an alcohol solvent (95%) three times heavier than the weight medicine for 60 minutes, after which time the medicine is placed into a oven at 70° C. temperature till the water content thereof becomes less than 12%. Then, the aflatoxin content is measure again, and we find it is 0 ppb.

Regarding the aflatoxins in the specimen of dried citrus peel in the third preferred embodiment, the precise amount is measured by a High Performance Liquid Chromatography, the difference in aflatoxin content before and after the process is shown in FIG. 5.

The present invention is thus described, and it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for removing aflatoxins from Chinese herbal medicines, comprising steps of:

(A) grinding a predetermined Chinese herbal medicine and submerging it into an amount of alcohol solvent twice as much as the dry weight of the medicine; and (B) using water to flush away the alcohol solvent from the medicine after a being submerged for predetermined period of time; and wherein said Chinese herbal medicine is Corydalis yanhusuo.

2. The method for removing aflatoxins from Chinese herbal medicines of claim 1 wherein said ground Chinese herbal medicine becomes powder at least larger than those particles capable of passing a 20 mesh sifting screen.

3. The method for removing aflatoxins from Chinese herbal medicines of claim 1 wherein said alcohol solvent has a concentration from 60%-95%.

4. The method for removing aflatoxins from Chinese herbal medicines of claim 1 wherein said predetermined period of time for submergence is at least 20 minutes.

5. The method for removing aflatoxins from Chinese herbal medicines of claim 1 further including the step of washing and grinding said Chinese herbal medicine.

6. The method for removing aflatoxins from Chinese herbal medicines of claim 1 further including the step of reducing the water content of said Chinese herbal medicine to be less than 12% after the removal of said solvent.

7. The method for removing aflatoxins from Chinese herbal medicines of claim 5 further including the step of reducing the water content of said Chinese herbal medicine to be less than 12% after the removal of said solvent.

8. The method for removing aflatoxins from Chinese herbal medicines of claim 1 further including the step of repeating steps (A) and (B) at least twice.

* * * * *